United States Patent [19]
Bolz et al.

[11] Patent Number: 5,609,611
[45] Date of Patent: Mar. 11, 1997

[54] PACEMAKER SYSTEM WITH POROUS ELECTRODE AND RESIDUAL CHARGE OR AFTER-POTENTIAL REDUCTION

[75] Inventors: Armin Bolz; Max Schaldach, both of Erlangen, Germany

[73] Assignee: Biotronik Mess-und Therapiegeraete GmbH & Co. Ingenieurbuero Berlin, Berlin, Germany

[21] Appl. No.: 403,723

[22] PCT Filed: Sep. 16, 1993

[86] PCT No.: PCT/DE93/00887

§ 371 Date: Mar. 17, 1995

§ 102(e) Date: Mar. 17, 1995

[87] PCT Pub. No.: WO94/06508

PCT Pub. Date: Mar. 31, 1994

[30] Foreign Application Priority Data

Sep. 17, 1992 [DE] Germany .......................... 42 31 603.0

[51] Int. Cl.[6] ........................................ A61N 1/36
[52] U.S. Cl. .................... 607/13; 607/9; 607/11; 607/16; 128/697; 128/704; 128/708
[58] Field of Search ....................... 607/9, 11, 13, 607/16, 63, 122, 126, 128; 128/901, 704, 708, 697

[56] References Cited

U.S. PATENT DOCUMENTS

| | | |
|---|---|---|
| 4,343,312 | 8/1982 | Cals et al. . |
| 4,373,531 | 2/1983 | Wittkampf et al. . |
| 4,406,286 | 9/1983 | Stein . |

(List continued on next page.)

FOREIGN PATENT DOCUMENTS

| | | |
|---|---|---|
| 0000989 | 3/1979 | European Pat. Off. . |
| 0126981 | 12/1984 | European Pat. Off. . |
| 2334357 | 1/1974 | Germany . |

(List continued on next page.)

OTHER PUBLICATIONS

M. Schaldach et al.: "Titannitrid–Herschrittmacher–Elektroden". In: Biomedizinische Technik, vol. 34, No. 7–8/1989, pp. 185–190.

A. Ripart et al.: "Electrode–Heart Interface: Definition of the Ideal Electrode". In: PACE, vol. 6, Mar.–Apr. 1983, Part II, pp. 410–421.

E. Alt: "Schrittmachertherapie des Herzens". In: 2. Auf–lage, perimed Fachbuch–Verlags GmbH, Erlangen, 1989, pp. 26–39.

H. J. Th. Thalen et al.: "Evoked Response Sensing (ERS) as Automatic Control of the Pacemaker Output". In: Cardiac Pacing, Piccin Medical Books, Padova 1982, pp. 1229–1234.

M. Spicer et al.: "Cardiac stimulator for the study of refractory period control using current pulses of programmable duration and shape". In: Medical & Biological Engineering & Computing, Jul. 1992, pp. 377–384.

Primary Examiner—Marvin M. Lateef
Assistant Examiner—Shawna J. Shaw
Attorney, Agent, or Firm—Spencer & Frank

[57] ABSTRACT

A cardiac pacemaker system is provided which includes a stimulation electrode adapted for being anchored in the heart. An output capacitor is coupled to the stimulation electrode. A first circuit coupled to the output capacitor generates stimulation pulses. A second circuit coupled to the output capacitor generates an autoshort pulse following each stimulation pulse to reduce a residual charge of the output capacitor for eliminating an after potential following a stimulation pulse by the stimulation electrode. A third circuit coupled to the output capacitor acquires an evoked pulse of the heart from an electrical signal picked up by the stimulation electrode. The stimulation electrode includes a porous surface coating made of an inert material and has an active surface that is substantially larger than a surface of the basic geometric form of the stimulation electrode. The second circuit includes circuit means for changing the time duration of the autoshort pulses as a function of the acquisition of the evoked pulses, with the time duration of the autoshort pulses being limited to 70 ms.

19 Claims, 6 Drawing Sheets

U.S. PATENT DOCUMENTS

| | | |
|---|---|---|
| 4,498,478 | 2/1985 | Bourgeois . |
| 4,542,752 | 9/1985 | DeHaan et al. . |
| 4,784,160 | 11/1988 | Szilagyi . |
| 4,858,610 | 8/1989 | Callaghan et al. . |
| 5,267,568 | 12/1993 | Takara . |
| 5,417,716 | 5/1995 | Franberg et al. . |
| 5,423,866 | 1/1995 | Ekwall . |
| 5,423,870 | 1/1995 | Olive et al. . |
| 5,480,441 | 1/1996 | Hudrlick . |
| 5,486,201 | 1/1996 | Canfield . |
| 5,556,420 | 9/1996 | Mortazavi et al. . |

FOREIGN PATENT DOCUMENTS

| | | |
|---|---|---|
| 2342030 | 3/1975 | Germany . |
| 2520729 | 11/1975 | Germany . |
| 2619001 | 11/1977 | Germany . |
| 3237198 | 4/1984 | Germany . |
| 3345990 | 6/1985 | Germany . |
| 3501169 | 7/1986 | Germany . |
| 3725125 | 2/1988 | Germany . |
| 4126363 | 2/1993 | Germany . |
| 4207368 | 2/1993 | Germany . |

PACEMAKER SYSTEM WITH POROUS ELECTRODE AND RESIDUAL CHARGE OR AFTER-POTENTIAL REDUCTION

BACKGROUND OF THE INVENTION

The invention relates to a cardiac pacemaker system of the type including a stimulation electrode adapted for being arranged in the heart; an output capacitor coupled to the stimulation electrode; a first circuit, coupled to the output capacitor, for generating a pulse following each stimulation pulse for at least one of reducing a residual charge of the output capacitor and eliminating an afterpotential following a stimulation pulse by the stimulation electrode; and a third circuit, for acquiring an evoked heart action from an electrical signal picked up by an electrode arranged in the heart.

For a long time, it has been a goal in the development of artificial cardiac pacemakers to verify the success of a heart stimulation through the measurement and evaluation of signals, which can be picked up in the heart on the basis of the evoked heart action via an electrode which is installed in the heart—and preferably the stimulation electrode itself.

The pickup of the electrical "response signal" of the heart after a stimulation is disturbed by the aftereffects of the stimulation pulse, which are caused by the polarization of the stimulated tissue, which can be reduced only when the recharging of the output (coupling) capacitor connected to the stimulation pulse is also eliminated.

This follows from the fact that the evoked potential, which indicates the success of the stimulation and is present at the heart approximately up to 300 ms after the stimulation, is superposed by an afterpotential in the order of magnitude of more than 10 mV. The afterpotential, which disturbs the effectiveness for recognition of the evoked potential, is caused by the effect of the stimulation electrode as an electrochemical electrode, from which results a saturation of the detection amplifier.

Apart from various circuits, with which attempts are made to eliminate the consequences of the afterpotential, an apparatus for the stimulation of the heart is known from EP-B1-0 000 989, wherein the disturbing afterpotential of the stimulation electrode is intended to be reduced in an accelerated manner by means of an additional, transistor-controlled resistor branch, which essentially short-circuits the Helmholtz capacity. The total time needed for the reduction of the disturbing afterpotential, however, is too long with customary electrodes to make possible an effective effectiveness recognition under all circumstances.

SUMMARY OF THE INVENTION

Starting from the drawbacks of the prior art, it is the object of the invention to provide a cardiac pacemaker system of the generic type mentioned in the introduction, in which an effective detection of evoked heart signals is possible in an effective manner, also under the different changing operating conditions of a cardiac pacemaker, which occur, for example, during the settling in of the electrode.

The above and other objects are accomplished in the context of a cardiac pacemaker system of the type first described above, wherein according to the invention the stimulation electrode includes a porous surface coating made of an inert material and having an active surface that is substantially larger than a surface of the basic geometric form of the stimulation electrode; and the pacemaker system includes circuit means for changing the time duration of the activation of the second circuit as a function of the acquisition of the evoked heart action, with the time duration of the activation of the second circuit being limited to no more than 70 ms.

The invention includes the finding that when an electrical voltage is applied to a pacemaker electrode, which is anchored in the heart, two layers of different charge carriers are formed, which, however, are separated by a monolayer of hydrogen molecules based on hydration effects. In its structure and electrical behavior, this so-called Helmholtz double layer corresponds to a plate capacitor. If, during the stimulation of the heart, a current flows via this Helmholtz capacity, a voltage is generated there which forms the afterpotential, with the voltage increasing as the Helmholtz capacity decreases. The afterpotential is additionally increased through further electrochemical reactions with charged reaction products taking place at the phase boundary. Apart from the increase of the Helmholtz capacity, a reduction of the stimulation pulse amplitude, above all, is important for reducing the afterpotential so that a definitive effectiveness recognition can be carried out with the same electrode. In addition, a reduction of the amplitude of the stimulation pulse contributes in an advantageous manner to increasing the service life of the pacemaker's current supply source.

The selection of the measures according to the invention can thus, on the one hand, reduce the stimulation pulse amplitude so that the afterpotential as a whole becomes lower. Moreover, the reduction of the afterpotential is accelerated so that the afterpotential is reducible in a defined manner within a predetermined period of time.

This reduction can take place by means of an active counterpulse or also through passive means at the output of the stimulation circuit, as is known from the prior art that was mentioned (autoshort).

According to advantageous modifications of the invention, it becomes possible through automatically operating circuit means to automatically determine the time duration of the blocking of the input amplifier for the evoked pulses and to adapt it to the implantation conditions or their temporal change. In this process, an increased stimulus energy is used, which, with certainty, leads to a stimulation.

Additionally, in an advantageous modification, a cardiac pacemaker system can be provided, which overall only has a low energy requirement because of the automatic adjustment of the stimulation amplitude.

It was recognized here that
- while a stimulation pulse having an excessive amplitude leads with certainty to a stimulation of the myocardium, the service life of the pacemaker's current supply source, however, is considerably reduced because of the increased energy consumption so that an early reimplantation must be carried out,
- a sufficiently reliable detection of evoked signals, based on a myocardium stimulation that has taken place, is possible only after a sufficient reduction of the afterpotential, which occurs due to the stimulation pulse, if stimulation and detection are carried out with the same electrode,
- the afterpotential may, at most, reach such a value which can be reduced to a negligible level within a period of approximately 30 to 80 ms (autoshort), before an evoked potential has decayed and
- the materials of the known electrodes and, in particular, titanium, vanadium, zircon and niobium tend to, at times, show extreme oxidation and that, in case of contact with aqueous electrolytes, this high oxidation tendency leads to the formation of a thin, insulating or semiconductive oxide layer at the electrode surface, with the oxide layer representing a capacity $C_{ox}$ connected in series with the Helmholtz capacity $C_H$ and thus leading to a slow reduction of the total capacity and therewith to the corresponding increase of the respectively required stimulation energy.

The pulse control of the control system according to the invention is configured both for the automatic determination of the width of the autoshort pulses, which is necessary for the detection of evoked potentials, and for maintaining a minimum amplitude of the stimulation pulses, which exceeds the stimulus threshold of the myocardium at the determined necessary width of the autoshort pulses, and it is provided with the electrical means necessary for this purpose. These essentially comprise a controllable autoshort pulse generator, a generator for the generation of amplitude-controlled stimulation pulses controlled by a gate circuit at a predetermined pulse repetition frequency and devices for the detection of the potentials evoked by the stimulation pulses as a function of the width of the autoshort pulses. The automatic setting of the autoshort time is among the most essential advantages of the pulse control.

The operation of the pulse control circuit represented here takes place in two different operating conditions, "alignment" and "continuous operation". According to the preferred embodiment of the invention, a pulse generator is provided for the generation of the autoshort pulses, in which a variation of the pulse width in the "alignment" operating condition is carried out in a scanning manner by a ramp generator. In this process, the stimulation pulses are kept constant with regard to their amplitude through a corresponding setting in the pulse amplitude control of the stimulation pulse generator, at a level which is above the stimulus threshold of the myocardium and at which an evoked potential is released with certainty. The correspondingly detected, pulse-shaped signals are fed to a memory after sufficient amplification.

The memory is configured in a matrix fashion or array fashion and is addressed by the above-mentioned ramp generator such that an allocation of the memory locations to the evoked signals takes place as a function of the respective autoshort pulses of a certain width.

An evaluation unit downstream of the matrix memory determines the most effective detection of the evoked potentials with respect to the pulse width of the autoshort pulses. This autoshort time is fixed in the generator for the autoshort pulses and sets as a self-adjusted value the width of the autoshort pulses for the "continuous operation" operating condition of the pulse control following the "alignment" operating condition. For the change-over of the operating conditions, a cyclical timer switch is provided by means of which the ramp generator, the generator for the autoshort pulses and the amplitude control stage of the stimulation pulses can be correspondingly switched on or off. During the "continuous operation" of the pulse control, a gate circuit, which is provided at the input of the amplitude control stage for the stimulation pulses, is activated by the timer switch and the detection pulses of the evoked potentials.

Each pulse that corresponds to a detected potential leads to a reduction of the amplitude of the stimulation pulses by a certain amount. If, after a number of stimulations, the stimulation pulse remains below the stimulus threshold, an evoked potential can no longer be picked up. A corresponding output signal at a gate circuit leads to an increase of the amplitude of the stimulation pulses in the downstream amplitude control stage to the value that was last applied successfully. This accomplishes that the stimulation pulse, which follows the missing detection of an evoked potential, leads with certainty to a renewed stimulation of the myocardium and that a "falling-out-of-step" of the synchronization of the total system is prevented.

It is evident that, instead of the stimulation amplitude, also the pulse width or another value that determines the stimulus energy can be changed.

It is also particularly advantageous if the afterpotential is compensated through an active counterpulse, because the electrode used in the cardiac pacemaker system according to the invention can also be operated anodically, without an oxide layer impairing the stimulation threshold.

According to an advantageous modification of the invention, the amplitude increase in case of a missing detection of an evoked potential is a multiple of the value of the amplitude decrease when a detection took place. This is accomplished in a simple manner by means of a divider circuit, which provides the output signals of the gate circuit for the amplitude reduction with this factor.

According to another advantageous embodiment of the invention, a change of the switching conditions of the timer switch takes place in time intervals of equal length, which cyclically repeat themselves, in order to regularly carry out a control of the selected autoshort time. It has proven advantageous to again carry out an "alignment" after a predetermined number of lowering cycles of the amplitude of the stimulation pulses until a potential detection first fails to appear so as to adjust the autoshort time, if necessary, to a possible change of the ability of the myocardium to be stimulated.

The function of the pulse control according to the invention is only guaranteed for autoshort times in the range of 50 ms if the constructive configuration of the stimulation electrode accomplishes that only a relatively low afterpotential is built up following the stimulation pulse.

According to the preferred embodiment of the invention, the stimulation electrode is provided with a porous surface coating made of an inert material, with the active surface of the coating being considerably larger than the surface that results from the geometric shape of the electrode. Because of the fractal spatial geometry, the active surface is so large that the energy required for the stimulation can be set to a minimum value. Thus, because of the electrodes' large relative surface, a successful stimulation with low energy is possible, in principle, for the conventional coated, porous electrodes. It was now recognized that the Helmholtz capacity is reduced due to the oxidation tendency, which leads to an increase in the electrode impedance. The reason why the influence, which is thus generated, on the electrode properties in the course of the implantation time is so serious is that the deterioration of the electrode properties has consequences which, in turn, contribute to the fact that the stimulation properties are also influenced adversely.

Thus, for a deteriorating electrode, a greater pulse energy is necessary so that, for the effectiveness recognition, a counterpulse with a greater energy requirement is also necessary which, in turn, again contributes to the deterioration of the electrode properties. Since the pulse energy and the counterpulses necessary for the effectiveness recognition are set to values that have to have validity over the total implantation time of the pacemaker, the deterioration of the operating conditions ultimately is essentially based on measures, which are actually intended to counteract the deteriorated operating conditions.

The long-term-stable, biocompatible surface coating of the stimulation electrode according to the invention is made of a material whose oxidation tendency is very low, with the coating being applied on the electrode using vacuum technology, preferably by using an inert material, namely a nitride, carbide, carbonitride or a pure element or certain alloys from the group gold, silver, platinum, iridium, titanium or carbon. Owing to the fractal spatial geometry of a surface layer applied in this manner, its active surface is very large so that the amount of energy needed for the stimulation can be kept extremely low.

The afterpotential of a stimulation electrode made of titanium, which is provided with a sputtered iridium nitride layer or titanium nitride layer by means of the reactive cathode sputtering, is smaller by up to six times (from approximately 600 mV to approximately 100 mV) than the afterpotential of a bare stimulation electrode made of titanium. Owing to this significant reduction of the afterpotential, the recognition of the intracardiac ECG is possible not only in the conventional manner by means of an amplifier and a triggering device, but an operative effectiveness recognition can be applied, which can do without counterpulse and autoshort times for the reduction of the afterpotential in the magnitude of 50 ms.

Advantageous modifications of the invention are described below in greater detail in conjunction with the accompanying Figures.

DETAILED DESCRIPTION OF THE PREFERRED EMBODIMENTS

Figure 1:
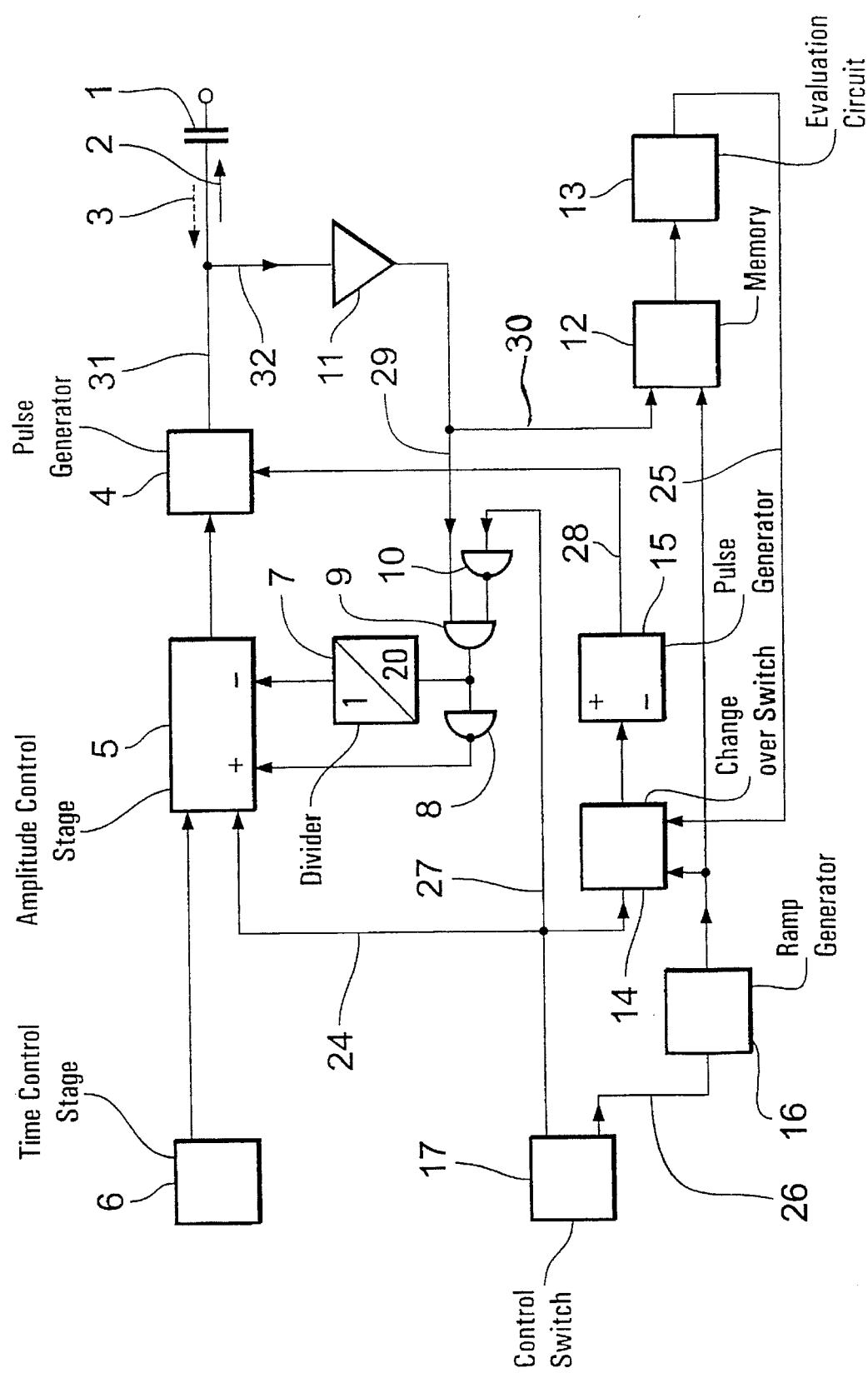
FIG. 1 is a block diagram of the preferred embodiment of the invention.

The means for the pulse generation of the control system according to the invention are schematically illustrated in FIG. 1. The stimulation electrode, which is part of the control system, is connected to the output capacitor 1 and is not shown in the drawing.

The electrode is provided with a pulse generator 4 for stimulation pulses that are released in the direction 2 onto the stimulation electrode.

A time control stage 6 determines the point in time of the release of stimulation pulses and, in this case, corresponds to a fixed frequency pacemaker. The schematic circuit diagram is also usable for other pacemaker circuits, where merely additional control lines must be provided, through which, for example, in a demand pacemaker, stimulation is prevented through the release of stimulation pulses in case of signals stemming from heart actions that come in before the end of the so-called escape interval. With an amplitude control stage 5, the amplitude (or the energy) of the stimulation pulses can be raised ("+") or lowered ("−") via additional inputs.

In addition, a pulse generator 15 is provided for the generation of autoshort pulses via the final pulse generator stage 4. Via a galvanic connection or an active counterpulse, the potential of the inner connection of the capacitor 1 is returned in this process to the initial state prior to the last stimulation pulse so that, by way of the charge shift generated, the afterpotential at the electrode is counteracted. The time duration of the pulse for eliminating the aftereffects of the stimulation pulse can be set via a corresponding input of the pulse generator 15.

Via an amplifier 11, signals that are generated by the heart are picked up, with the amplifier being switched so as to be insensitive by switching means, that are not shown, when a stimulation pulse occurs. An evoked event is retained in a memory 12. In order to be able to optimize the time duration of the autoshort pulse, a signal indicating an evoked event is retained in allocation to the duration of the corresponding autoshort pulse.

The "alignment" operating mode is set by means of a control switch 17 while, otherwise, the circuit is in the "continuous operation" operating mode.

During the "alignment" operating condition, the optimum autoshort time is determined, which is then maintained in the "continuous operation" position. For this purpose, a pulse amplitude is predetermined by the timer switch 17 via the control line 24 in the amplitude control 5 at a constant frequency (time control 6), at which pulse amplitude an evoked potential at the myocardium is generated with certainty. Simultaneously, the timer switch 17 activates, via the control line 26, a ramp generator 16, which is connected to the pulse generator 15 via a change-over switch 14 to vary the width of the autoshort pulses in in a scanning manner. The AND gate 9 is blocked, also controlled by way of the timer switch 17 via the line 27 and a negator 10.

A picked up evoked potential or a corresponding signal 3 indicating this condition is fed to an amplifier 11 via the connecting line 32 and acquired in a matrix memory 12. The allocation of the individual memory locations takes place in dependence of the time function of the ramp generator 16 so that to each pulse width a signal can be allocated, which indicates the pickup of an evoked potential. An evaluation circuit 13 determines the most favorable autoshort time for the detection of the evoked potentials 3. In this process, a mean value of all pulse durations of the autoshort pulse, at which an evoked potential could be picked up, is selected so as to have a certain amount of certainty with respect to the change of the signal pickup conditions in the course of the operating time of the pacemaker.

Subsequently, the switch 17 is reset to the "continuous operation" operating condition, during which process the mean value of the autoshort time, at which an evoked potential could be picked up, is retained in the pulse generator 15 via the change-over switch 14 and the line 25, and the AND gate 9 is released via the negator 10. Afterwards, the stimulation amplitude is again lowered to its normal value.

It is now possible with the evoked potentials, which can be recognized reliably because of the alignment that was carried out, to set the stimulation energy (stimulation amplitude) during the operation with threshold control via an effectiveness recognition in such a way that the stimulation threshold is reliably exceeded without a premature exhaustion of the energy source occurring because of an excessive stimulation energy.

Each detection of an evoked potential 3 generates a pulse via the AND element 9 at the divider 7, which pulse decreases the amplitude of the next stimulation pulse 2 by a certain amount. This step-by-step amplitude reduction takes place until no evoked potential is detected at the predetermined autoshort time. The level change at the output of the AND gate 9 switches the negator 8 and then effects a raising of the stimulation amplitude up to a preceding value at which a stimulation took place reliably. Via the divider 7, an amplitude decrease only takes place at every nth (here 20. This value only represents an example, because, in practice, the stimulus threshold will stabilize in the long term so that divider ratios of several thousand will be practicable.) successful stimulation pulse—but a raising immediately following every failed stimulation. Thus, the stimulation pulses are always provided with a stimulus energy, in particular, amplitude, which is only slightly above the stimulus threshold, respectively leading to a heart stimulation with great certainty.

In order to acquire possible changes in the transmission ratios of the myocardium, it is of particular advantage after a "continuous operation" phase of the pulse control to again determine the autoshort time, which is optimal for the stimulation and detection of the heart activity, in a repetition of the "alignment." It has proven advantageous to carry out a further "alignment" for the amplitude of the stimulation pulses after a "continuous operation" with, for example, m-cycles. In addition, it is possible to adjust the change-over cycle of the switch 17 to the patient-specific conditions.

Figure 2:
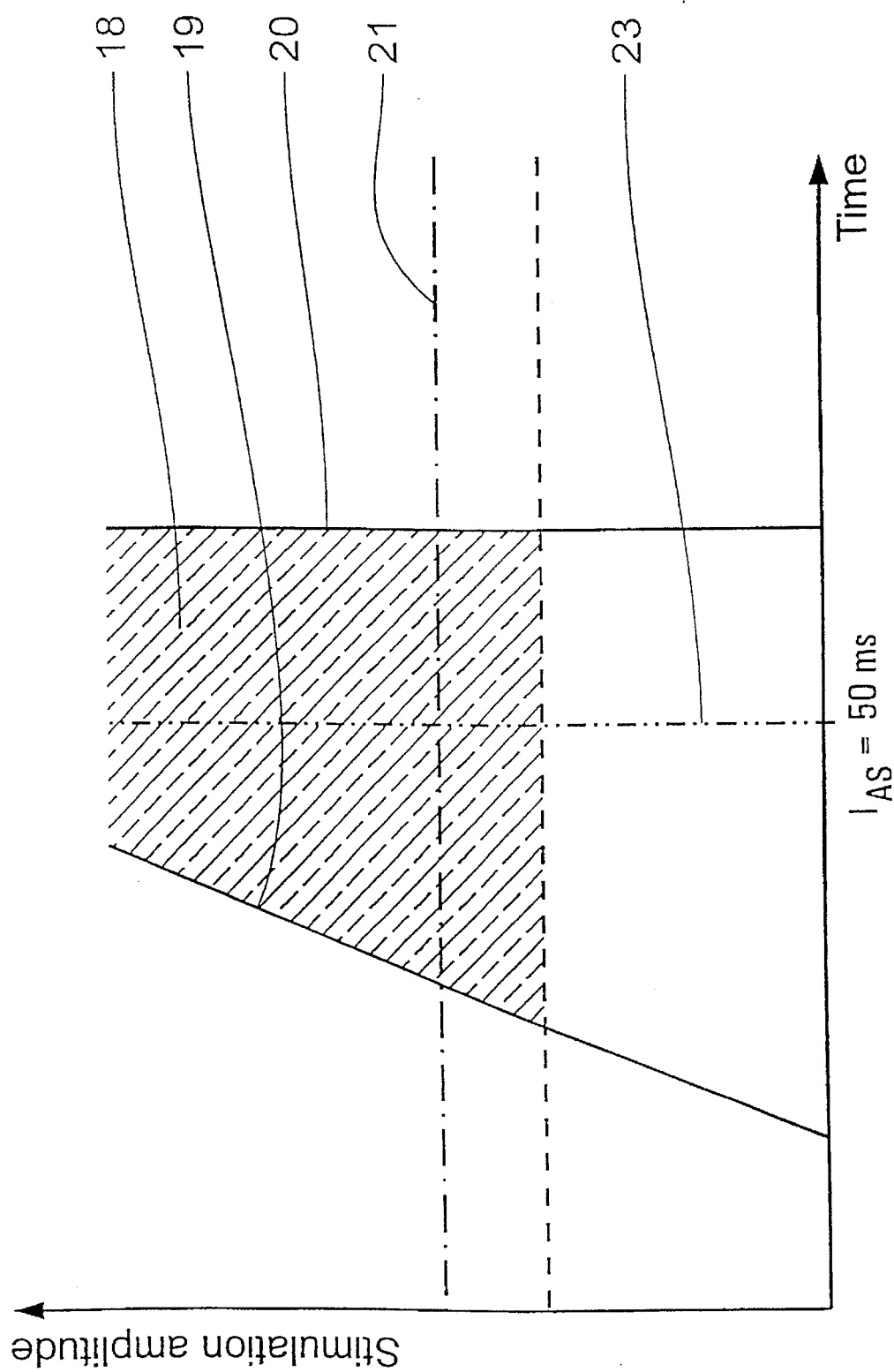
FIG. 2 is an overview diagram containing the most important influencing quantities for the pulse control in a schematic representation.

The schematically illustrated diagram of FIG. 2 shows, on the time axis, the possibility of picking up evoked potentials in the heart as a function of the variation of the autoshort time and of the stimulation amplitude.

Evoked signals can only be picked up if a stimulation pulse is effective, which means that the pulse has exceeded a predetermined threshold energy, as it is indicated by the horizontal line 21. In addition, the possibility of the pickup of evoked signals is further limited by the decay of the evoked potential, which is indicated by line 19 as limit for the decay of the stimulation effect (afterpotential). The line has a slight gradient, because, with a higher stimulation amplitude, the (disturbing) afterpotential also increases or the duration of its decay becomes longer. The point in time 20 forms that time mark after which an evoked potential has decayed to such a low level that its detection is no longer possible or the event of interest has passed. With the measures according to the invention, a time range for the measures to eliminate the afterpotential is set during an automatic adjustment of the duration of the autoshort time, this time range being within the effective range. Between the limit values generated by the lines 19 and 20, in particular, a mean value is set. The coating of the stimulation electrode according to the invention makes possible a lowering of the afterpotential, which disturbs the detection of the evoked potentials, at an autoshort time of 50 ms to a value of almost 0 mV (compare FIG. 7).

Figure 3:
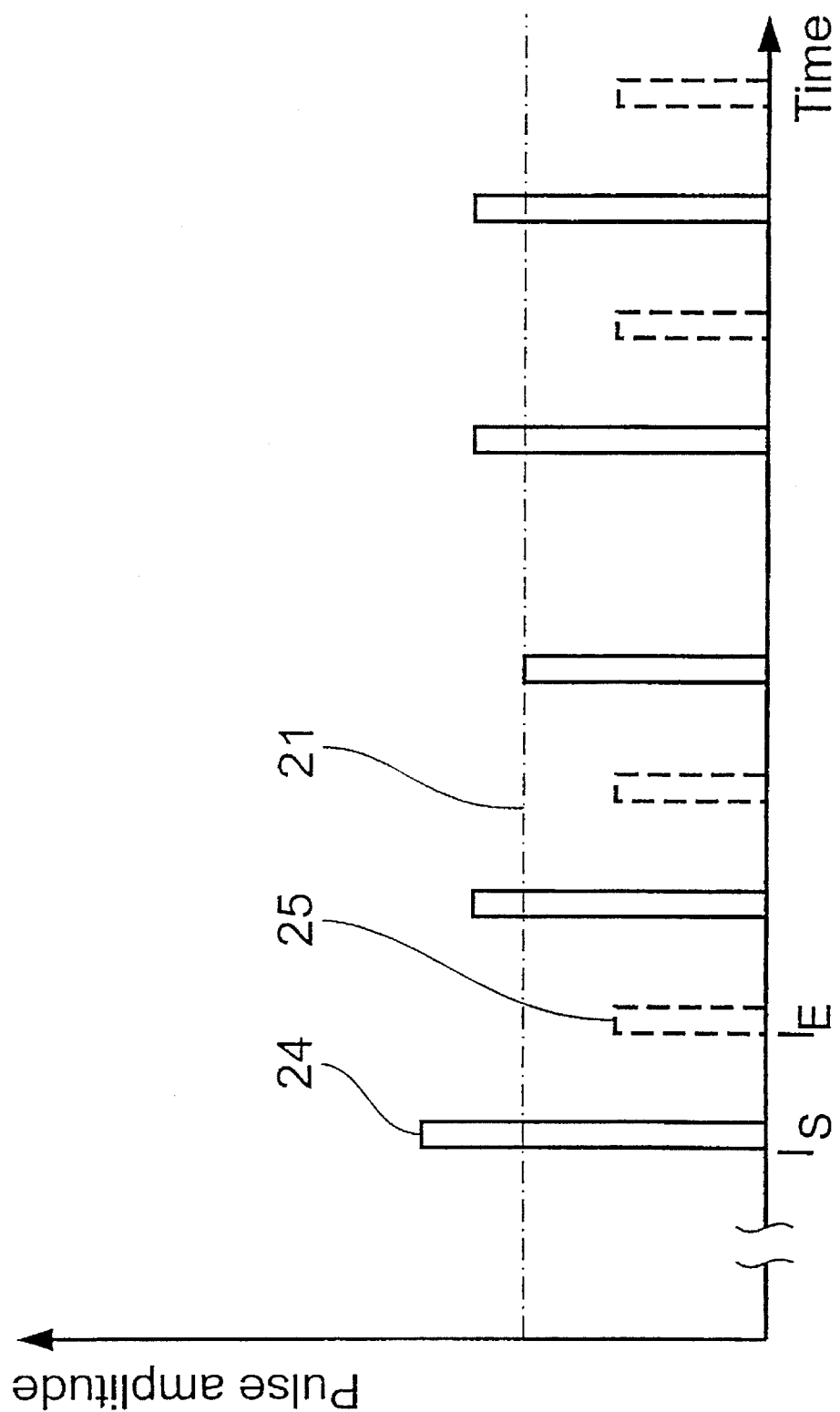
FIG. 3 is an amplitude-time diagram, shown schematically, for the generated stimulation pulses and the detected evocation potentials.

FIG. 3 shows the amplitude-time-diagram of the stimulation pulses 24 in relation to detectable evoked potentials 25 during the "continuous operation" operating condition of the pulse control. After each stimulation pulse 24, for which an evoked potential 25 is detected after the autoshort time $T=t_E-t_S$, a step-by-step amplitude reduction takes place via the pulse amplitude control (compare position 5 in FIG. 1). If the detection limit with the stimulus threshold 21 is reached or if a slight shortfall occurs, the resulting change in potential at the output of the gate circuit (comprising elements 7, 8, 9, 10 in FIG. 1) effects a renewed increase of the amplitude of the subsequent stimulation pulse 24. The amplitude jump occurs, in particular, to the amplitude value at which a successful stimulation has last taken place.

In order to keep the number of shortfalls of the stimulus threshold, at which effective stimulation does not occur, as low as possible, a lowering is only carried out at every nth stimulation pulse in advantageous embodiments of the invention, with a raising immediately following every threshold shortfall.

Figure 4:
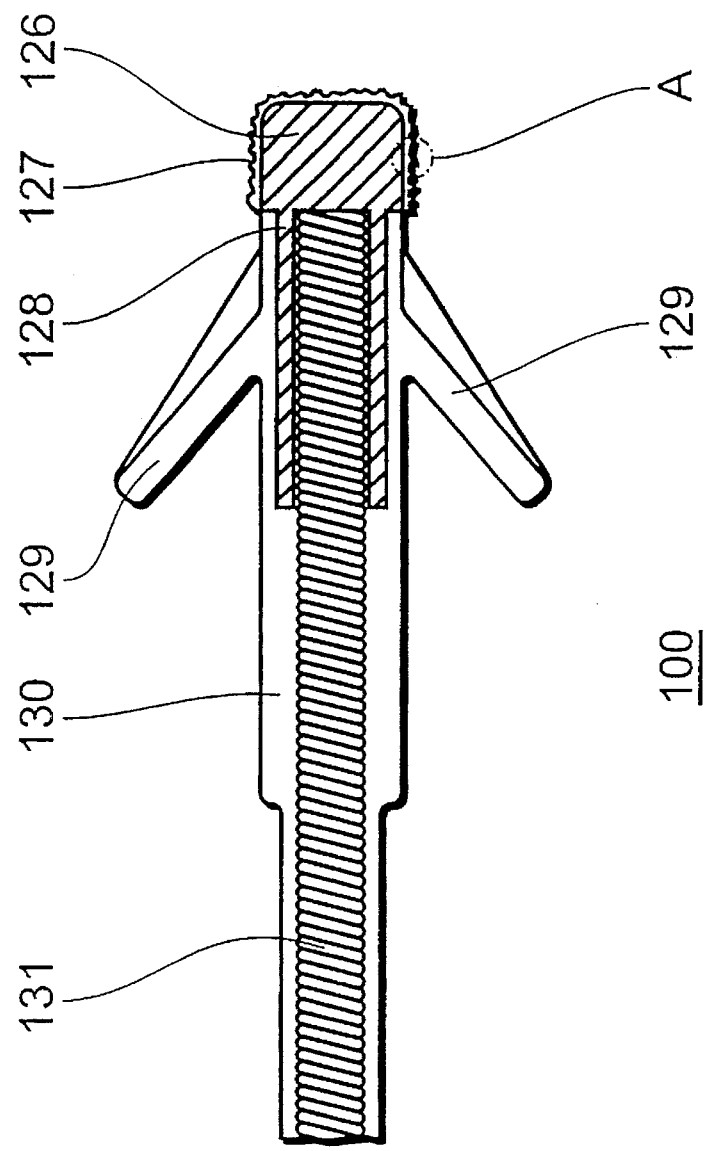
FIG. 4 is an embodiment of a stimulation electrode represented schematically in side view.

The stimulation electrode 100, illustrated in FIG. 4 in a schematic side view, is a unipolar nap electrode having a head that is provided with a cylinder-shaped basic body 126 made of titanium. The cylinder-shaped basic body 126 is provided with a surface coating 127 consisting of an inert material iridium nitride (IrN), which is applied to the cylinder-shaped basic body 126 of the titanium electrode by means of cathode sputtering. The electrode is provided with a coiled electrically conductive lead 131, which is provided with an electrically insulating sheathing 130 made of silicon. This silicon sheathing is shown to be transparent in the drawing. Formed to the silicon sheathing are flexible fastening elements 129 oriented rearward, which serve to anchor the electrode in the heart, with the surface of the basic body being kept in contact with the inner heart surface.

By means of a hollow-cylindrical shoulder 128, the basic body 126 is slid over the lead 131 and fastened there, with this shoulder being shown in sectional view in the drawing.

Figure 5:
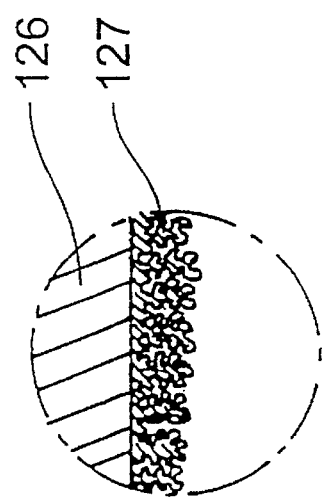
FIG. 5 is an enlarged representation of detail A in FIG. 4 in a sectional view.

FIG. 5 is an enlarged view of a section (detail A in FIG. 4) of the active surface. As is evident from the illustration, the fractal spatial geometry (enlarged not to scale) of the coating 127, grown in the microscopic range in a stem-like manner, accomplishes an essential enlargement of the active surface. The surface enlargement achieved is in the range of more than 1000.

Figure 6:
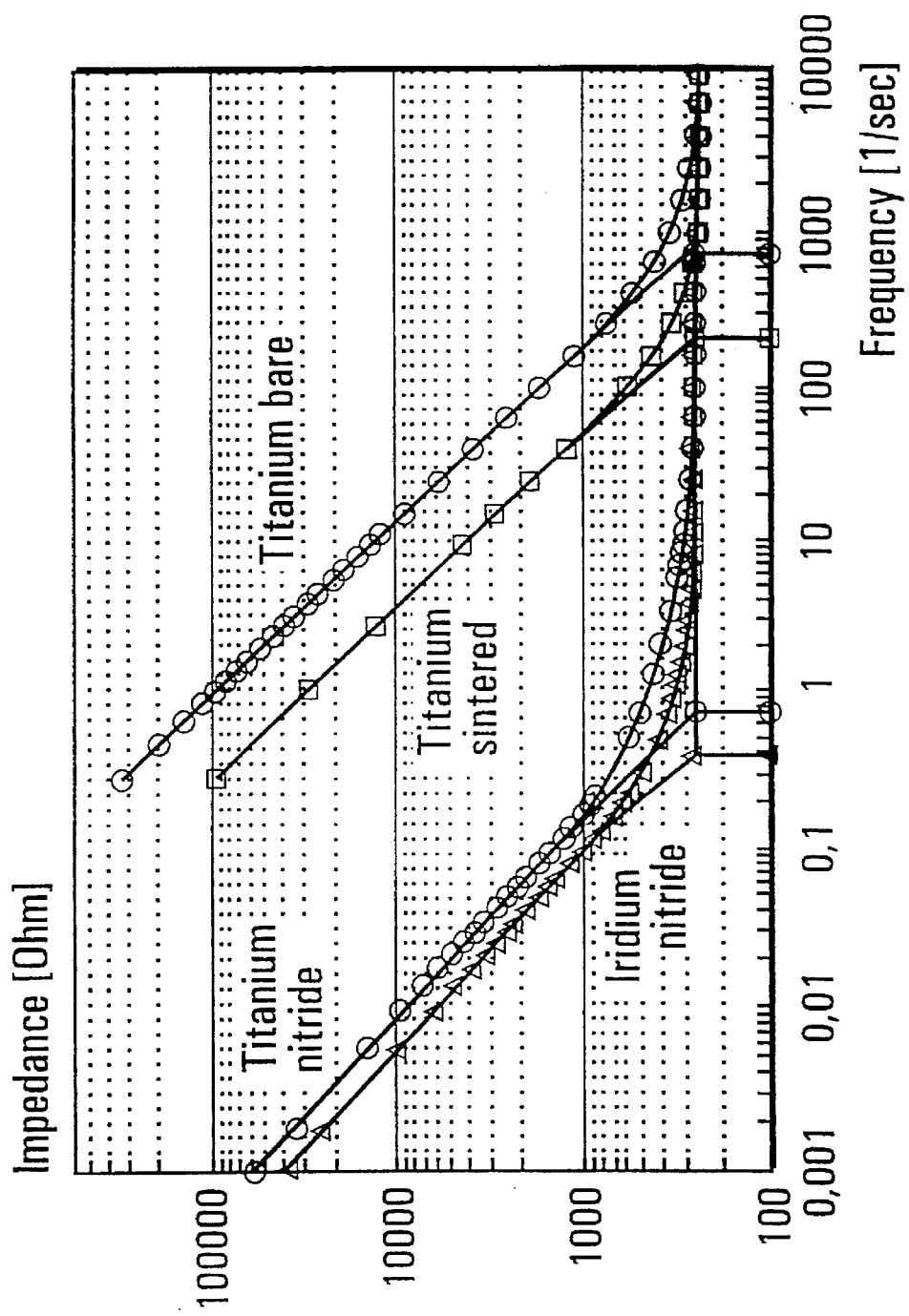
FIG. 6 is a diagram to compare the impedance of the embodiment of the electrode with the impedance of corresponding electrodes known from prior art having the same geometric dimensions.

As can be seen from FIG. 6, which shows a comparison of the impedance curves of stimulation electrodes having different surface coatings, an electrode which is coated with iridium nitride has the lowest phase boundary impedance for picking up heart signals for which the low-frequency range is particularly important, especially in the region where the signals are weak, as compared to titanium or titanium nitride which are recognized state of the art electrode surface materials. The differences determined are particularly essential in their consequences for the reason that the amplitude of the picked up signal is related in a square function to the internal resistance of the signal source.

Figure 7:
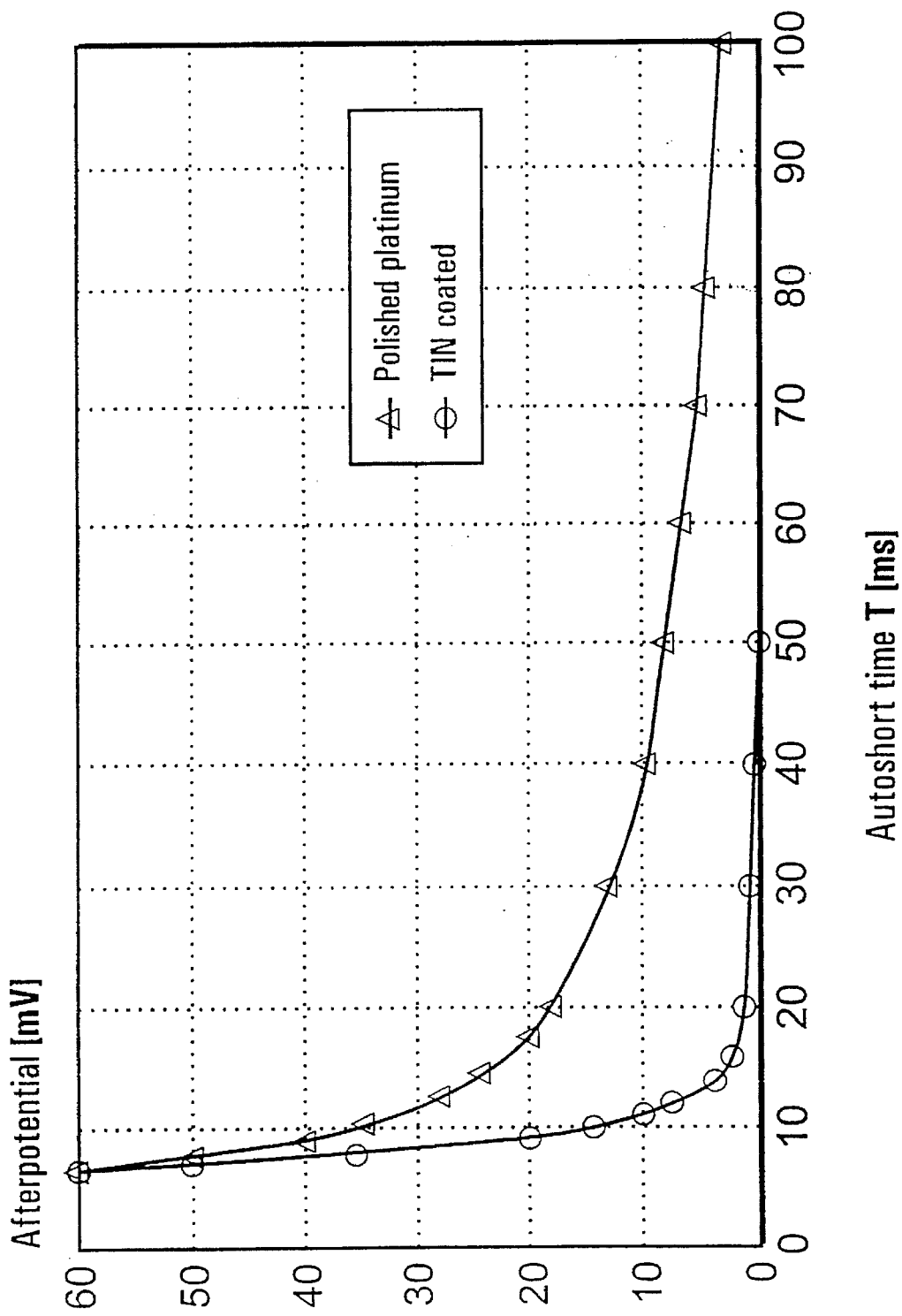
FIG. 7 is a representation of the afterpotential as a function of the autoshort time in dependence of the surface configuration of the electrode.

FIG. 7 illustrates the measurement results, which show the afterpotential generated by the stimulation as a function of the autoshort time T in dependence of the configuration of the stimulation electrode. Since the evoked potential indicating the success of a myocardium stimulation can be found in a time range of 50 to 300 ms after the stimulation, its detection can occur without disturbance with a titanium-nitride-coated stimulation electrode at autoshort times of 50 ms, whereas the evoked potential is "covered" by afterpotentials in the magnitude of 10 mV in uncoated platinum electrodes. This also makes the detection of the evoked potentials at a point in time after 50 ms considerably more difficult and is not possible with uncoated stimulation electrodes, since the amplitude of the evoked potential reduces itself very quickly after generation and drops below the level of the remaining afterpotential.

The invention is not limited in its implementation to the preferred embodiment described above. On the contrary, a number of variants are conceivable which utilize the described solution, also if the embodiments are, in principle, of a different type.

We claim:

1. A cardiac pacemaker system including: a stimulation electrode adapted for being arranged in the heart; an output capacitor coupled to the stimulation electrode; a stimulation circuit, coupled to the output capacitor, for generating stimulation pulses; a pulse-generating circuit, coupled to the output capacitor, and being activated for generating a pulse following each stimulation pulse for at least one of reducing a residual charge of the output capacitor and eliminating an afterpotential following a stimulation pulse by the stimulation electrode; and an evoked response circuit, coupled to a control input of the pulse generating circuit, for acquiring an evoked heart action from an electrical signal picked up by an electrode installed in the heart, the improvement wherein:

the stimulation electrode includes a porous surface coating made of an inert material and having an active surface that is substantially larger than a surface of the basic geometric form of an uncoated stimulation electrode; and the pacemaker system includes circuit means for changing a time duration of the activation of the pulse generating circuit as a function of the acquisition of the evoked pulses, with the time duration of the activation being limited to no longer than 70 ms.

2. The cardiac pacemaker system of claim 1, wherein the time duration of the activation of the pulse generating circuit is no longer than 50 ms.

3. The cardiac pacemaker system of claim 1, wherein the circuit means for changing the time duration of the activation of the pulse generating circuit automatically sets the time duration during an alignment period in which, with an amplitude of the stimulation pulses at a raised level, the time duration of the activation of the pulse generating circuit is successively varied between individual stimulation pulses until an evoked heart action is acquired by the evoked response circuit.

4. The cardiac pacemaker system of claim 3, wherein the circuit means for changing the time duration of the activation of the pulse generating circuit reduces the time duration of the activation, starting from a maximum value.

5. The cardiac pacemaker system of claim 3, wherein the circuit means for changing the time duration of the activation of the pulse generating circuit includes means for raising the amplitude of the stimulation pulses, means for varying the time duration of the activation of the pulse generating circuit and means for storing the acquisition of each evoked heart action in allocation to a respective time duration of the activation of the pulse generating circuit.

6. The cardiac pacemaker system of claim 3, and further including means connected to the stimulation circuit for changing the amplitude of the stimulation pulses to a level which assures reliable acquisition of an evoked heart action by the evoked response circuit after the automatic setting of the time duration.

7. The cardiac pacemaker system of claim 6, wherein the means for changing the amplitude of the stimulation pulses includes a regulating circuit for reducing the amplitude of the stimulation pulses by a first predetermined amplitude amount if an evoked heart action is detected by the evoked response circuit and for increasing the amplitude of the stimulation pulses by a second predetermined amplitude amount if no evoked heart action is detected by the evoked circuit, wherein the regulating circuit is operative when the circuit means for changing the time duration of the activation of the pulse generating circuit is inoperative.

8. The cardiac pacemaker system of claim 7, wherein the first predetermined amplitude amount is smaller than the second predetermined amplitude amount.

9. The cardiac pacemaker system of claim 7, wherein the means for changing the amplitude of the stimulation pulses is operative for reducing the amplitude of the stimulation pulses by the first predetermined amount at every nth detection of an evoked heart action by the evoked response circuit.

10. The cardiac pacemaker system of claim 1, and further including an addressable memory connected to the evoked response circuit for storing the acquisitions of evoked heart actions.

11. The cardiac pacemaker system of claim 5, wherein the circuit means for changing the time duration of the activation of the pulse generating circuit includes a ramp generator for producing a ramp output signal, and the means for storing the acquisition of the evoked heart actions comprises an addressable memory which allocates the acquisition of evoked heart actions to memory locations as a function of the ramp output signal.

12. The cardiac pacemaker system of claim 11, wherein the circuit means for changing the time duration of the activation of the pulse generating circuit includes an evaluation unit coupled to the addressable memory for determining a mean time duration for the activation of the pulse generating circuit at which evoked heart actions are acquired and fixing the time duration of the activation of the pulse generating circuit to the mean duration during a continuous operating mode.

13. The cardiac pacemaker system of claim 12, wherein the circuit means for changing the time duration of the activation of the pulse generating circuit includes a change-over switch coupled to the pulse generating circuit for connecting the pulse generating circuit in the alignment period with the ramp generator and for coupling the pulse generating circuit in the continuous operation mode with the evaluation unit.

14. The cardiac pacemaker system of claim 1, wherein the active surface of the stimulation electrode has a fractal spatial geometry and is larger by a factor of at least one thousand than the surface comprising the basic geometric form of the stimulation electrode.

15. The cardiac pacemaker system of claim 1, wherein the inert material is selected from a group comprising a nitride, carbide, carbonitride and a pure element or alloy selected from the group comprising gold, silver, titanium, iridium, platinum and carbon.

16. The cardiac pacemaker system of claim 1, wherein the porous surface coating is applied to the stimulation electrode by a thin-film technology.

17. The cardiac pacemaker system of claim 16, wherein the thin-film technology comprises one of reactive cathode sputtering and ion plating.

18. The cardiac pacemaker system of claim 1, wherein the stimulation electrode has a basic body comprised of titanium on which the porous surface coating is applied.

19. The cardiac pacemaker system of claim 1, wherein the electrode for picking up an electrical signal of an evoked heart action comprises the stimulation electrode.

* * * * *